(12) United States Patent
Nakamura

(10) Patent No.: US 7,454,950 B2
(45) Date of Patent: Nov. 25, 2008

(54) VEHICLE EXHAUST GAS ANALYZER

(75) Inventor: Hiroshi Nakamura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/277,681

(22) Filed: Mar. 28, 2006

(65) Prior Publication Data

US 2006/0236752 A1  Oct. 26, 2006

(30) Foreign Application Priority Data

Mar. 29, 2005  (JP) .................. 2005-096055
Apr. 4, 2005  (JP) .................. 2005-108032

(51) Int. Cl.
*G01N 7/00* (2006.01)
(52) U.S. Cl. ................... 73/23.31; 73/23.32
(58) Field of Classification Search ........... 73/23.31, 73/23.32
See application file for complete search history.

(56) References Cited

U.S. PATENT DOCUMENTS

| 3,882,028 | A | | 5/1975 | Zolner |
| 3,958,122 | A | | 5/1976 | Jowett et al. |
| 5,385,974 | A | * | 1/1995 | Ohmae et al. ............ 525/58 |
| 5,731,510 | A | * | 3/1998 | Jones et al. ............ 73/23.31 |
| 5,846,831 | A | | 12/1998 | Silvis et al. |
| 6,151,952 | A | * | 11/2000 | Mathews et al. ......... 73/23.31 |
| 6,701,706 | B2 | * | 3/2004 | Bruck et al. ............ 60/276 |
| 6,823,368 | B1 | * | 11/2004 | Ullmann et al. ......... 709/206 |
| 6,865,472 | B2 | * | 3/2005 | Nakamura ............... 701/108 |
| 2004/0064243 | A1 | * | 4/2004 | Nakamura ............... 701/114 |
| 2005/0032232 | A1 | | 2/2005 | Silvis et al. |

FOREIGN PATENT DOCUMENTS

| EP | 0076834 B1 | 10/1987 |
| EP | 0936467 A2 | 8/1999 |
| EP | 1 106 983 A | 6/2001 |
| EP | 1106983 A | 6/2001 |
| EP | 1405989 A2 | 4/2004 |
| GB | 2368125 A | 4/2002 |
| JP | 61-151446 | 7/1986 |
| JP | 06-167450 | 6/1994 |
| JP | 11-230869 | 8/1999 |
| JP | 2002-005838 | 1/2002 |

OTHER PUBLICATIONS

Partial European Search Report; Application No. EP 06 00 6674; Sep. 19, 2006; European Patent Office.

(Continued)

*Primary Examiner*—Michael Cygan
(74) *Attorney, Agent, or Firm*—Brooks Kushman P.C.

(57) ABSTRACT

An exhaust gas analyzer includes a main flow path and at least one sub-flow path. Exhaust gas from an internal combustion engine is introduced to the main flow path; sub-flow paths are parallel to the main flow path. Plural kinds of analyzers are mounted on the main flow path and sub-flow paths to measure concentration of multiple components in the exhaust gas. Actual measurement values of the concentration for the measured components are obtained. A deviance from a true value generated to an actual measurement value due to a mutual influence of the measured components is corrected based on at least one actual measurement value.

9 Claims, 3 Drawing Sheets

OTHER PUBLICATIONS

European Search Report, application No. EP06006674, Feb. 26, 2007.
European search report dated May 8, 2008.
Ridley et al., An Instrument For Nitric Oxide Measurements In The Stratosphere, rev. Sci. Instrum., vol. 45, No. 6, Jun. 1974, pp. 742-746.
Steffenson et al., Optimization Of The Operating Parameters Of Chemiluminescent Nitric Oxide Detectors, Analytical Chemistry, vol. 46, No. 12, Oct. 1974, pp. 1704-1709.
European search report dated Apr. 2, 2008.

* cited by examiner

VEHICLE EXHAUST GAS ANALYZER

BACKGROUND OF THE INVENTION

1. Field of the Invention

This invention relates to a multiple component gas analyzer that analyzes various components contained in exhaust gas from vehicles.

2. Background Art

Conventionally, various gas analyzers are used in order to measure components in exhaust gas discharged from a vehicle such as an automobile. For example, as shown in Japan Patent laid open no. 11-230869, an infrared gas analyzer is used in order to measure the concentration of CO or $CO_2$ and a chemiluminescence nitrogen oxide analyzer is used in order to measure the concentration of $NO_X$. In addition, a hydrogen flame ionization analyzer to measure the concentration of THC (total hydro carbon) is also well-known.

With these analyzers, other components in the exhaust gas cause interference or quenching to the component as an object to be measured due to a system of these analyzers, thereby causing an error in the measurement result. As a result, for example, a detector for correcting interference or quenching is arranged separately inside of the infrared gas analyzer. In addition, in order to reduce quenching due to $CO_2$ or $H_2O$, the chemiluminescence nitrogen oxide analyzer diminishes the flow rate of the exhaust gas to take, dilutes the exhaust gas in advance or raises a degree of vacuum.

However, in case that interference is caused due to multiple components for the chemiluminescence nitrogen oxide analyzer, it is necessary to provide multiple detectors to correct interference for each component, resulting in complicated arrangement. In addition, if the flow rate of the exhaust gas is decreased or the exhaust gas is diluted for the chemiluminescence nitrogen oxide analyzer, the sensitivity or the precision is degraded, and the response of the measurement is also affected. If the degree of vacuum is raised, a large-size vacuum pump is necessary.

These problems such that the arrangement becomes complicated or large, or the measurement sensitivity, the measurement accuracy and the response of the measurement are degraded are a bottleneck for developing an exhaust gas analyzer that can be mounted on a vehicle and that can measure the exhaust gas continuously on a real time basis.

In addition, a conventional vehicle-mountable exhaust gas analyzer is provided with a heated piping or dehumidifier to remove moisture in order to prevent an adverse influence on the exhaust gas analyzer due to moisture ($H_2O$) contained in the exhaust gas, however, the heated piping or dehumidifier consumes a lot of electric power. This becomes a bottleneck for making the exhaust gas analyzer vehicle-mountable.

More specifically, the conventional exhaust gas analyzer is so arranged that the sample gas is introduced into each analyzer through the introductory piping. Since CO, $CO_2$, $NO_X$, THC as being an object to be measured are mixed with $H_2O$ in the sample gas discharged from the above emission source, if the introductory piping is not heated, the moisture ($H_2O$) in the sample gas condenses inside the introductory piping. If the condensation is caused, volume of the sample gas decreases and the concentration of the component as the object to be measured is calculated to be higher. As a result, the conventional exhaust gas analyzer uses a heated introductory piping provided with a heater as the introductory piping for the exhaust gas.

In addition, in case that the moisture is contained in the sample gas when measuring the concentration of CO and the concentration of $CO_2$ by an NDIR analyzer, if CO is the component as the object to be measured, moisture contained in the sample gas causes moisture interference because an absorption wavelength region of the infrared light due to CO is close to an absorption wavelength region of the infrared light due to moisture ($H_2O$), thereby to have an influence on the measurement value of CO analysis. Furthermore, if the moisture concentration in the sample gas is not stable, the influence of the moisture concentration also changes, which might cause an error in the measurement value of CO.

A CLD type $NO_X$ analyzer detects light of the ultraviolet region by a photo sensor and detects the concentration of $NO_X$ in a sample from a luminescence amount in a certain space to which the sample is introduced by making use of a nature that the luminescence amount varies in proportion to an amount of $NO_X$ molecule.

At this time, it is known that the luminescence amount decreases if moisture ($H_2O$) or $CO_2$ exists. This is a phenomenon called as quenching, and influences a measurement value of $NO_X$. Furthermore, if the moisture concentration in the sample gas is not stable, the influence of the moisture concentration also changes, which might cause an error in the measurement value of $NO_X$.

Then a conventional exhaust gas analyzer is provided with a dehumidifier in order to solve problems of the moisture interference for the NDIR analyzer, the quenching for the CLD type $NO_X$ analyzer and the unstable moisture concentration.

However, the heated piping or dehumidifier arranged for a conventional vehicle-mountable exhaust gas analyzer in order to solve the above-mentioned problems resulting from the moisture ($H_2O$) contained in the exhaust gas consumes a lot of electric power. The power consumption consumed by the heated piping or the dehumidifier occupies greater part of the electric power consumed by the exhaust gas analyzer. (Japan Patent laid open no. 2002-5838.)

Conventionally, an exhaust gas analyzer to analyze component contained in exhaust gas discharged from a vehicle is generally of a type installed in an indoor laboratory. Then the exhaust gas has been analyzed during a driving experiment in the indoor laboratory. However, as a recent interest concerning an influence of the component contained in the exhaust gas on environment or human health has been growing, it is desired to analyze the exhaust gas discharged from the vehicle while the vehicle is actually driving on a road.

In order to make it possible to mount the exhaust gas analyzer on a vehicle, the exhaust gas analyzer has to be downsized, weight saved and electric power saved. However, since the conventional exhaust gas analyzer is provided with the heated piping or the dehumidifier whose electric consumption is big in order to exclude the adverse influence due to moisture existing in the exhaust gas, it is difficult to save the electric power.

SUMMARY OF THE INVENTION

It is an object of the invention to provide an exhaust gas analyzer that can be downsize, and electric power saved, and that can conduct continuous measurement with high sensitivity on a real time basis.

More specifically, the exhaust gas analyzer in accordance with this invention is characterized by comprising a main flow path to which exhaust gas discharged from an internal combustion engine is continuously introduced in a chronological order, one or multiple sub-flow path(s) furcated from the main flow path and arranged in parallel to the main flow path, plural kinds of analyzers some of which are mounted on the main flow path and others of which are mounted on the sub-flow path(s) and that measure concentration of each of multiple components as an object to be measured in the exhaust gas in a chronological order, an actual measurement value obtaining part that obtains an actual measurement value of the concentration for each component as the object to be measured in the exhaust gas discharged at the same time based on a difference between times until the exhaust gas reaches each analyzer, and a correction part that corrects a deviance from a true value generated to a part or all of each actual measurement value due to a mutual influence of the components as the object to be measured based on a part or all of each actual measurement value.

In accordance with this arrangement, since the influence due to interference or quenching of components measured by each analyzer is mutually corrected by the use of the measured values, there is no need of providing a detector for correction for exclusive use, thereby to downsize the exhaust gas analyzer and to save electric power. In other words, since it is possible to arrange the flow path system that measures the concentration of multiple different kinds of gas continuously in a chronological order without dilution easily as much as possible, the exhaust gas analyzer can be downsized and electric power saved. In addition, it is possible to provide the exhaust gas analyzer that is superior in accuracy, response and sensitivity and that can conduct a measurement continuously on a real time basis.

As the component as the object to be measured, at least CO, $CO_2$, $H_2O$ and THC can be represented. In this case, it is preferable to provide an infrared gas analyzer to measure concentration of CO, concentration of $CO_2$, and concentration of $H_2O$ and a hydrogen flame ionization analyzer to measure concentration of THC as the analyzer. Then it is preferable that the correction part conducts intermediate correction on each actual measurement value concerning the concentration of CO, the concentration of $CO_2$, and the concentration of $H_2O$ based on the actual measurement value of the concentration of THC obtained by the hydrogen flame ionization analyzer, and the intermediate correction value of the concentration of CO and the intermediate correction value of the concentration of $CO_2$ are further corrected based on the intermediate correction value of the concentration of CO, the intermediate correction value of the concentration of $CO_2$ and the intermediate correction value of the concentration of $H_2O$.

In accordance with this arrangement, since it is possible not to require or to downsize a dehumidifier or a hot hose to reduce a moisture interference influence, the exhaust gas analyzer can be downsized and electric power saved. Furthermore, since the deviance of the time when the exhaust gas reaches each analyzer is corrected, an accuracy in measurement can be secured. In addition, the infrared gas analyzer can also measure the concentration of $H_2O$, an exclusive concentration meter to measure the concentration of $H_2O$ becomes unnecessary.

If the component as the object to be measured further includes $NO_X$ and a chemiluminescence nitrogen oxide analyzer to measure concentration of $NO_X$ is further provided, it is preferable that the correction part corrects the actual measurement value concerning the concentration of $NO_X$ based on a final correction value of the concentration of $CO_2$ and a final correction value of the concentration of $H_2O$.

Since the chemiluminescence nitrogen oxide analyzer does not need a process of diminishing a flow rate of the exhaust gas to import in order to reduce quenching due to $CO_2$ or $H_2O$, nor a process of diluting the exhaust gas in advance, the flow rate of the exhaust gas importing to the chemiluminescence nitrogen oxide analyzer can be increased at once, thereby to improve sensitivity and response of measurement. In addition, since high vacuum is unnecessary, the vacuum pump can be downsized.

Furthermore, if the infrared gas analyzer is arranged on the main flow path (the bypath) by making use of a fact that the flow rate of the exhaust rate to the infrared gas analyzer can be increased, a flow path exclusive for the infrared gas analyzer can be omitted, thereby to contribute to downsizing the exhaust gas analyzer.

If a sub-flow path that furcates from the main flow path is arranged and the chemiluminescence nitrogen oxide analyzer and the hydrogen flame ionization analyzer are arranged on the sub-flow paths, it is possible to introduce the exhaust gas into each analyzer as soon as possible and at the same time as much as possible. This arrangement enables the exhaust gas analyzer to continuously measure the concentration of the component as the object to be measured in the exhaust gas with high accuracy and high response.

In order to reduce a number of a vacuum pump as much as possible, it is preferable that a downstream end of the main flow path and downstream ends of the sub-flow paths are arranged to be sucked by a common pump.

In addition, a vehicle-mountable exhaust gas analyzer in accordance with this invention is characterized by being of a vehicle-mountable type that measures concentration of a component as an object to be measured such as $NO_X$, THC, CO and $CO_2$ contained in exhaust gas discharged from a vehicle, and comprising a drain separator connected to an exhaust duct of the vehicle through an unheated piping, a measuring instrument group that measures concentration of moisture in the exhaust gas and concentration of the component as the object to be measured in a semi-dry state wherein liquid moisture is removed by the drain separator, a dry concentration calculating part that calculates concentration of the component as the object to be measured in the exhaust gas in a dry state wherein moisture is completely removed based on the concentration of the moisture and the concentration of the component as the object to be measured obtained by the measuring instrument group, and an actual concentration calculating part that calculates concentration of the component as the object to be measured contained in the exhaust gas at a time when the exhaust gas is discharged from the vehicle based on the concentration of the component in the dry state and a predetermined conversion equation.

In accordance with this arrangement, since the unheated introductory piping is used, it is possible to reduce electric power consumption. In addition, since the drain separator is connected to the exhaust duct, the dew condensed moisture in the sample gas can be discharged outside. The drain separator here may remove just liquid moisture contained in the exhaust gas without complicated arrangement nor temperature adjustment. Furthermore, it is possible to calculate the dry concentration of the component as the object to be measured contained in the exhaust gas by measuring the concentration of the moisture remaining in the sample gas and the concentration of the component as the object to be measured by the use of the measuring instrument group. In addition, it is possible to calculate the concentration of the component as the object to be measured contained in the exhaust gas at the time when the exhaust gas is discharged from the vehicle by removing the influence due to the moisture contained in the exhaust gas based on the dry concentration by the use of the predetermined conversion equation. Then in accordance with the vehicle-mountable exhaust gas analyzer, it is possible to reduce electric power consumption and to calculate the concentration of the component as the object to be measured with high accuracy by eliminating the influence of the moisture contained in the exhaust gas.

More concrete arrangement of the vehicle-mountable exhaust gas analyzer of the present claimed invention represented is of a vehicle-mountable type that measures concentration of a component as an object to be measured such as $NO_X$, THC, CO and $CO_2$ contained in exhaust gas discharged from a vehicle, and that comprises a drain separator connected to an exhaust duct of the vehicle through an unheated piping, a measuring instrument group that includes an infrared gas analyzer to measure concentration of CO, concentration of $CO_2$ and concentration of $H_2O$, a chemiluminescence nitrogen oxide analyzer to measure concentration of $NO_X$, and a hydrogen flame ionization detector to measure concentration of THC, and that measures concentration of the component as the object to be measured in the exhaust gas in a semi-dry state wherein liquid moisture is removed by the drain separator, a dry concentration calculating part that calculates concentration of the component as the object to be measured in the exhaust gas in a dry state wherein moisture is completely removed based on the concentration of the component as the object to be measured and the concentration of $H_2O$ measured by the measuring instrument group, and an actual concentration calculating part that calculates concentration of the component as the object to be measured contained in the exhaust gas at a time when the exhaust gas is discharged from the vehicle based on the concentration of the component in the dry state and a predetermined conversion equation.

In order to further improve the electric power consumption, it is preferable that the drain separator alone is provided as a water removal mechanism, more specifically it is preferable that the vehicle-mountable exhaust gas analyzer is not provided with a dehumidifier whose electric power consumption is big.

If the dehumidifier or the heater is removed as much as possible, an error of the actual measurement value from the true measurement value due to mutual influence of the components as the object to be measured becomes remarkable. Then in order to solve this problem by the use of a software without complicated arrangement, it is preferable that a correction part that corrects a deviance from a true value generated to a part or all of each actual measurement value due to a mutual influence of the components as the object to be measured based on a part or all of each actual measurement value and that calculates true measurement value of the component as the object to be measured in a semi-dry state is further provided, and that the dry concentration calculating part calculates the concentration of each component as the object to be measured in the dry state based on the true measurement value obtained by the correction part.

As a preferable concrete embodiment, it is represented that the correction part conducts intermediate correction on each actual measurement value concerning the concentration of CO, the concentration of $CO_2$, and the concentration of $H_2O$ based on the actual measurement value of the concentration of THC obtained by the hydrogen flame ionization analyzer, and the intermediate correction value of the concentration of CO and the intermediate correction value of the concentration of $CO_2$ are further corrected based on the intermediate correction value of the concentration of CO, the intermediate correction value of the concentration of $CO_2$ and the intermediate correction value of the concentration of $H_2O$, and calculates a true measurement value for each component as the object to be measured in the semi-dry state by correcting the actual measurement value concerning the concentration of NO, based on the correction value of the concentration of $CO_2$ and the correction value of the concentration of $H_2O$.

As a result of this, it is possible to realize the exhaust gas analyzer of a vehicle-mountable type that can conduct a measurement continuously on a real time basis and that is superior in accuracy of measurement.

DETAILED DESCRIPTION OF THE PREFERRED EMBODIMENTS

An exhaust gas analyzer 100 in accordance with one embodiment of the present claimed invention will be described in detail with reference to the accompanying drawings.

Figure 1:
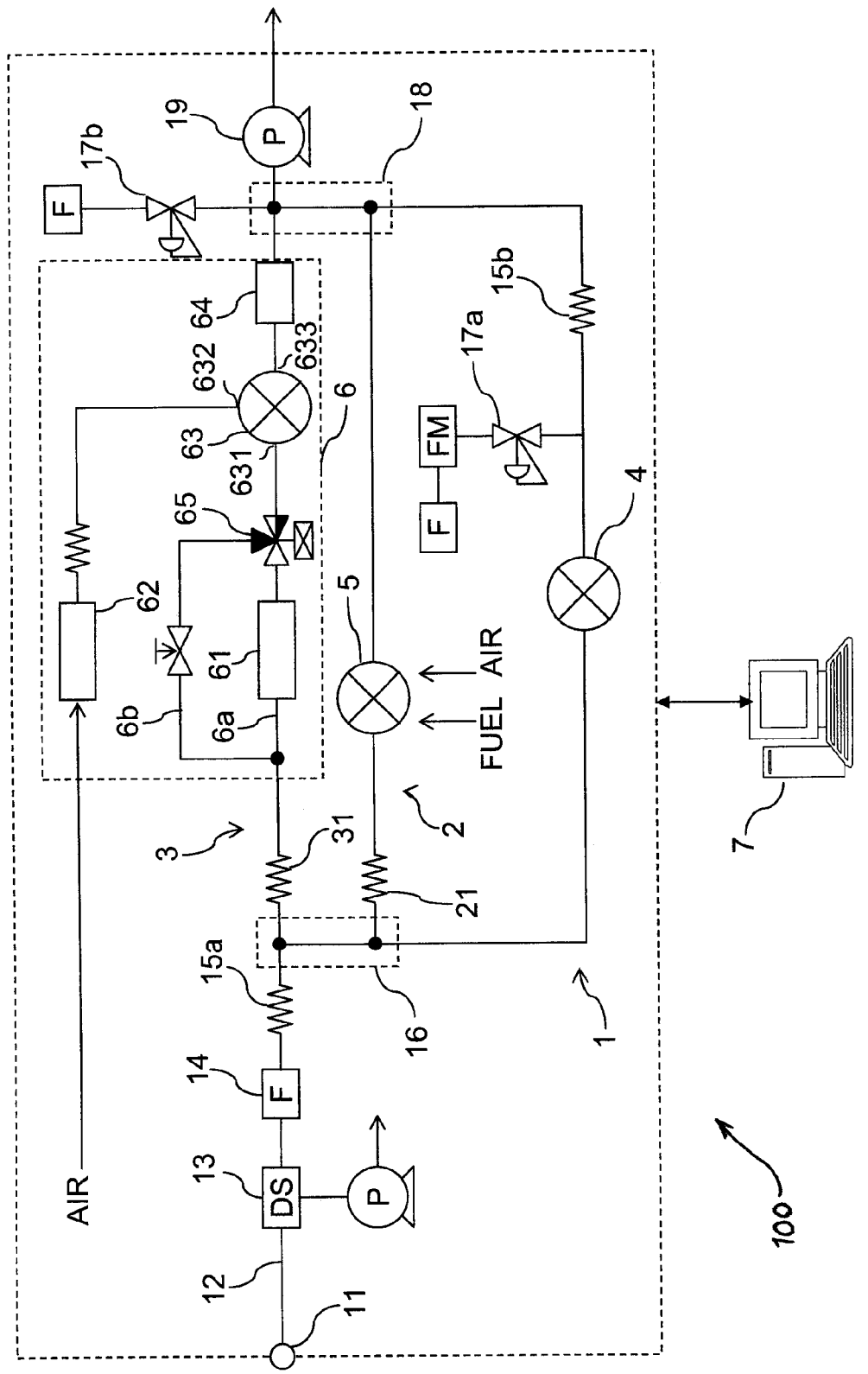
FIG. 1 is an overall fluid circuit diagram of an exhaust gas analyzer in accordance with one embodiment of the present claimed invention.

The exhaust gas measuring system 100 in accordance with this embodiment is to measure concentration of various components in exhaust gas while a vehicle is actually in motion with the exhaust gas measuring system 100 loaded on a trunk of the vehicle and, as shown in FIG. 1, comprises three different analyzers 4, 5, 6, a flow path system for supplying the exhaust gas continuously to the analyzers 4, 5, 6, and an information processing unit 7 that receives actual measurement data from each analyzer 4, 5, 6 and analyzes them, that calculates true measurement values, and that controls a valve arranged in the flow path system.

Each component will be described.

First, an infrared gas analyzer 4 to measure each concentration of CO, $CO_2$, $H_2O$, a hydrogen flame ionization analyzer 5 to measure concentration of THC, and a chemiluminescent nitrogen oxide analyzer 6 (hereinafter also called as a CLD type $NO_X$ analyzer 6) to measure concentration of $NO_X$ are used as the analyzers 4, 5, 6 in this embodiment.

The infrared gas analyzer 4 is of a nondispersive type and measures light intensity of each wavelength by a light detector at a time when infrared rays of characteristic wavelength which each CO, $CO_2$, $H_2O$ absorbs is irradiated on the sample gas (the exhaust gas) to pass through the sample gas, and outputs each of them. Then each of the output values is compared with a reference value at a time when no light is absorbed so that light absorbency of each wavelength can be calculated. Since the light absorbency corresponds to the concentration (the amount) of each component as an object to be measured, the concentration (the amount) of CO, $CO_2$, and $H_2O$ can be specified, however, a value of each light absorbency of CO, $CO_2$, and $H_2O$ does not correspond one-to-one with the concentration of CO, $CO_2$, and $H_2O$ since the light absorbency of CO, $CO_2$, and $H_2O$ is affected by interference of THC, and the concentration of CO, $CO_2$ is affected by mutual interference and interference of $H_2O$.

The hydrogen flame ionization analyzer 5 is of a type wherein fuel gas (hydrogen gas) is mixed into the sample gas (the exhaust gas) at a constant ratio, the mixed gas is burned, electric current generated due to ionization of THC contained in the sample gas is detected and output. Then the hydrogen flame ionization analyzer 5 can calculate an amount (concentration) of THC from the output value of the electric current.

In addition to the fuel gas, combustion supporting gas (air) also is introduced into the hydrogen flame ionization analyzer 5.

The CLD type $NO_X$ analyzer 6 converts all of $NO_X$ contained in the exhaust gas into NO by an NO converter 61, mixes NO with ozone output from an ozone generator 62 in a reaction vessel 63 so as to initiate a chemical reaction, detects luminescence intensity generated due to the chemical reaction by a light detector (not shown in drawings) and outputs it. Since the luminescence intensity corresponds to the concentration (the amount) of NO, it is possible to specify the concentration (the amount) of NO from the luminescence intensity. However, since $CO_2$ or $H_2O$ interferes (quenching) a phenomenon of the light emission during the chemical reaction, it is not true that the concentration of NO can be calculated instantaneously from the value of the luminescence intensity.

In this embodiment, in addition to a path 6a to introduce the exhaust gas into the reaction vessel 63 through the NO converter 61, a path 6b is arranged in parallel to the above path 6a to introduce the exhaust gas directly into the reaction vessel 63. Then the exhaust gas is introduced into the reaction vessel 63 alternatively only through either one of the parallel paths 6a, 6b so that the concentration of NO alone contained in the exhaust gas can be measured or the concentration of $NO_X$ except for NO also can be measured by obtaining differences. The ozone generator 62 imports atmospheric air without dehumidification. The numeral 64 denotes an ozone dehumidifier. The reaction vessel 63 is a box body having a certain volume and comprises a sample gas introducing port 631, an ozone-containing gas introducing port 632 and a leading-out port 633. The gas from either one of the parallel paths alternatively selected by the switch valve as mentioned above is introduced into the sample gas introducing port 631 and the ozone-containing gas from the ozone generator 62 is introduced into the ozone-containing gas introducing port 63.

The flow path system comprises a main flow path 1 that plays a role as a bypath to pass almost all of the exhaust gas, and multiple (two) sub-flow paths 2, 3 arranged in parallel and bifurcated from the main flow path 1. The infrared gas analyzer 4 is arranged on the main flow path 1, the hydrogen flame ionization analyzer 5 is arranged on one of the sub-flow paths 2 (a first sub-flow path 2) and the CLD type $NO_X$ analyzer 6 is arranged on other sub-flow path 3 (a second sub-flow path 3) respectively.

An upstream end of the main flow path 1 opens as a main port 11 and a suction pump 19 is arranged at the most downstream side of the main flow path 1. An exhaust duct of a vehicle is connected to the main port 11 and an amount of the exhaust gas required for measurement is introduced into the main flow path 1 by sucking the exhaust gas by the use of the suction pump 19.

More concretely, in succession to the main port 11 an introductory piping 12, a drain separator 13 to remove liquid moisture contained in the exhaust gas, a filter 14, a flow rate control pipe (capillary) 15a, a bifurcated part 16, the infrared gas analyzer 4, a flow rate control pipe (capillary) 15b, an interflow part 18, the suction pump 19 are arranged serially in this order. Since portions from the exhaust duct of the vehicle to the drain separator 13 are connected with an unheated piping alone at least without using a heated piping, the exhaust gas discharged from the vehicle is rapidly cooled to a normal temperature by the introductory piping 12, the moisture contained in the exhaust gas condensates and attaches to inside the introductory piping 12 as liquid moisture and the liquid moisture is discharged out of the introductory piping 12 through the drain separator 13. Then the exhaust gas in a state wherein only the liquid moisture is removed by the drain separator 13 (hereinafter also called as a semi-dry state) is introduced into each analyzer 4, 5, 6. A pressure control valve 17a connected downstream of the infrared gas analyzer 4 is to control the pressure in the flow path system between the capillaries 15a and 15b, and serves as a role to hold the flow rate and the pressure of the exhaust gas flowing into the infrared gas analyzer 4 constant in cooperation with each capillary 15, 15b.

The sub-flow paths 2, 3 are so arranged to be bifurcated from the main flow path 1 at the bifurcated part 16 and to be connected to the main flow path 1 again at the interflow part 18.

A flow rate control pipe (capillary) 21 and the hydrogen flame ionization analyzer 5 are arranged in this order on the first sub-flow path 2. The flow rate control pipe 21 is to limit the amount of gas that flows into the first sub-flow path 2 to a flow rate (very small amount compared with the flow rate of the exhaust gas that flows into the main flow path 1) necessary for measuring the concentration of THC.

A flow rate control pipe (capillary) 31 and the CLD type $NO_X$ analyzer 6 are arranged in this order from upstream on the second sub-flow path 3. The flow rate control pipe (capillary) 31 is to limit the amount of gas that flows into the second sub-flow path 3 to a flow rate (very small amount compared with the flow rate of the exhaust gas that flows into the main flow path 1) necessary for measuring the concentration of $NO_X$.

The pressure control valve 17b connected to the interflow part 18 is to control pressure of each sub-flow path 2, 3, and serves as a role to hold the flow rate and the pressure of the exhaust gas flowing into the hydrogen flame ionization analyzer 5 and the CLD type $NO_X$ analyzer 6 constant in cooperation with each capillary 21, 22 arranged upstream of each sub-flow path 2, 3.

Figure 2:
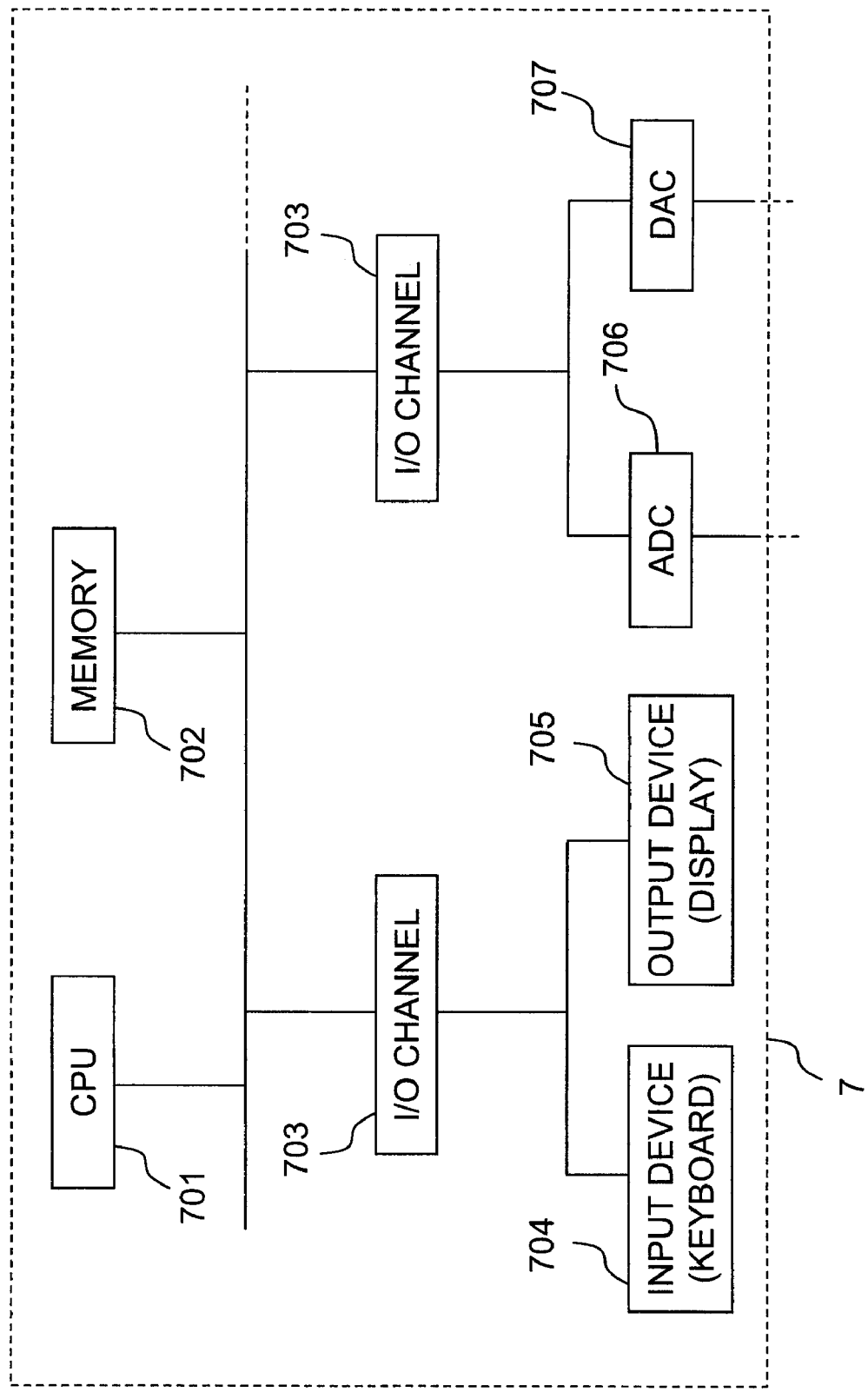
FIG. 2 is a circuit structure diagram of an information processing unit in accordance with this embodiment.

The information processing unit 7 is, as shown in FIG. 2, of multi-purpose or exclusive use comprising a CPU 701, a memory 702, an input/output channel 703, an input device 704 such as a keyboard, and a display 705. An analog-digital converting circuit such as an A/D converter 706, a D/A converter 707, and an amplifier (not shown in drawings) is connected to the input/output channel 703.

Figure 3:
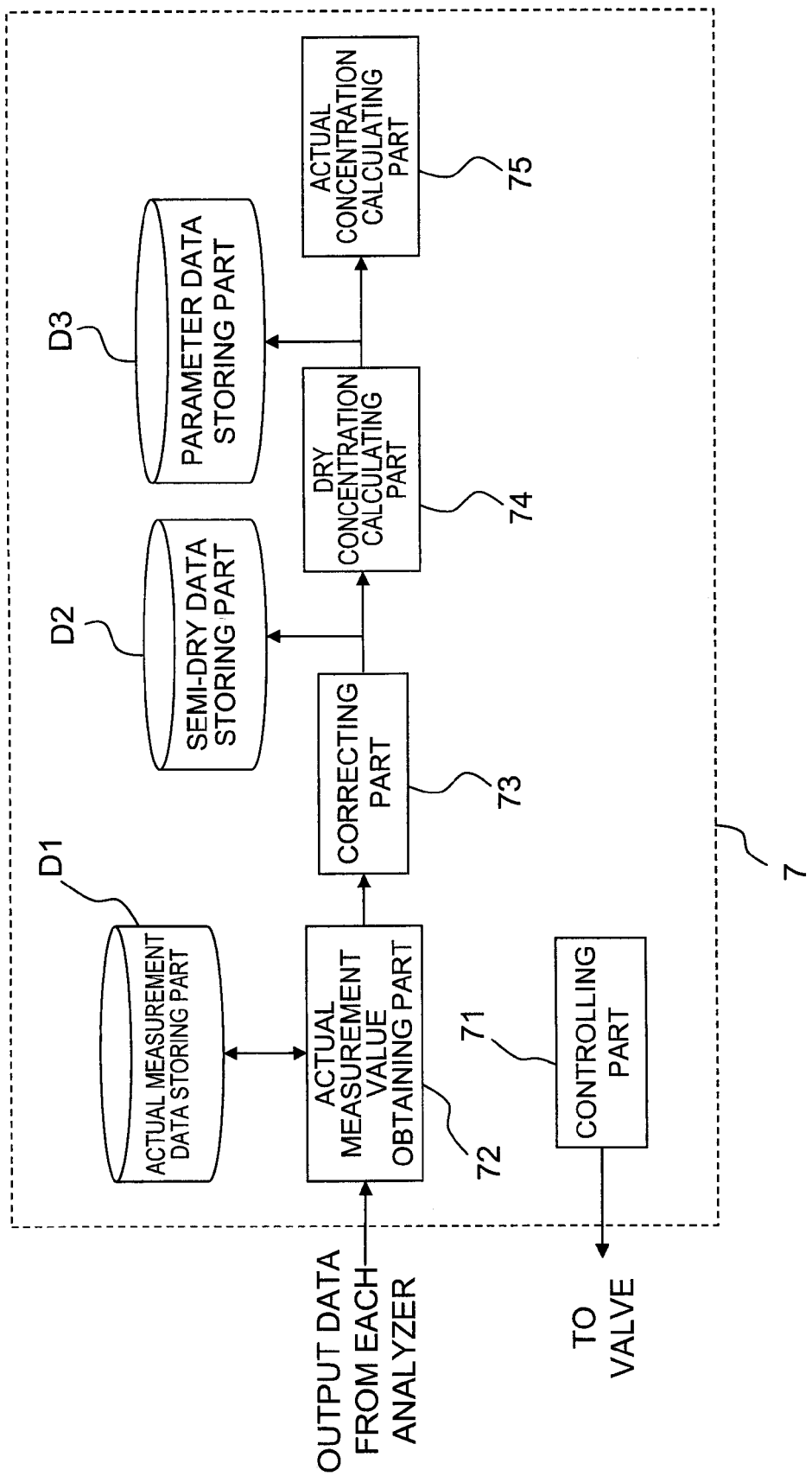
FIG. 3 is a functional block diagram of the information processing unit in accordance with this embodiment.

The information processing unit 7 at least fulfills function, as shown in FIG. 3, as a controlling part 71 that controls the valve arranged on the flow path system to open or close or temperature of a heater, and an actual measurement value obtaining part 72 that obtains each actual measurement value of the exhaust gas discharged at the same time by each analyzer 4, 5, 6, a correction part 73 that corrects a deviance from a true value generated to a part or all of each actual measurement value, a dry concentration calculating part 74 that calculates the concentration of the component as the object to be measured in the exhaust gas in a dry state wherein moisture is completely removed based on the correction value, and an actual measurement calculating part 75 that calculates the concentration of the component as the object to be measured contained in the exhaust gas at a time the exhaust gas is discharged from the vehicle based on the concentration of the component in the dry state and a predetermined conversion equation. The information processing unit 7 is not necessarily integrated physically, and may be separated into multiple instruments connected by a fixed line or wireless.

Each functioning part 71~75 will be explained.

The actual measurement value obtaining part 72 receives output data from each analyzer 4, 5, 6 by sampling at a predetermined interval, provides the output data with an average process, a gain process by an amplifier or a detector, or an offset process, if necessary, and stores the data as the actual measurement data in a chronological order in an actual measurement data storing part D1 set at a predetermined area in the memory. In addition, the actual measurement value obtaining part 72 memorizes in advance a deviance of a time between the times when the exhaust gas reaches each analyzer 4, 5, 6, extracts each actual measurement data concerning the exhaust gas discharged at the same time from the actual measurement data storing part D1 based on the deviance of the time and outputs them. For example, the actual measurement data of the exhaust gas that reaches either one of the analyzer 4, 5 or 6 at the latest time, and the other actual measurement data that is obtained by other analyzer 4, 5 or 6 at a time prior to the time when the above actual measurement data is obtained at the latest time by the deviance of the time are output at the time when the actual measurement data is obtained from the analyzer 4, 5 or 6 to which the exhaust gas reaches at the latest time.

The correction part 73 receives each actual measurement data output from the actual measurement data obtaining part 72, corrects each value shown by each actual measurement data, namely the actual measurement data concerning each component as the object to be measured based on a part or all of each actual measurement data, and outputs each corrected data showing its correction value. A concrete explanation is as follows.

First, the concentration of THC will be explained. The correction part 73 calculates the concentration of THC in a semi-dry state by providing the actual measurement value by the hydrogen flame ionization analyzer 5 with a zero/span calibration process and a linearlization process, and further pressure compensation and temperature compensation.

Next, the concentration of CO, the concentration of $CO_2$, and the concentration of $H_2O$ will be explained.

The correction part 73 provides the accrual measurement value by the infrared gas analyzer 4 with a first-order correction based on the concentration of the THC in the semi-dry state calculated from the above-mentioned actual measurement value of the THC concentration. The correction equation is as follows.

$$P_{CO} = O_{CO} - K_{HC(CO)} \cdot [\text{THCconc. (vol \%)}]$$

$$P_{CO2} = O_{CO2} - K_{HC(CO2)} \cdot [\text{THCconc. (vol \%)}]$$

$$P_{H2O} = O_{H2O} - K_{HC(H2O)} \cdot [\text{THCconc. (vol \%)}]$$

O: the actual measurement value

P: the first-order correction value (correction value wherein THC interference is excluded)

[THCconc. (vol %)]: the concentration of THC (in semi-dry state)

The subscript shows each value concerning CO, $CO_2$, $H_2O$.

Next, in order to further correct an influence by a mutual interference between CO and $CO_2$, each value of the CO concentration and the $CO_2$ concentration that is provided with the first-order correction is provided with a second-order correction based on each value. The correction equation is as follows.

$$Q_{CO} = (P_{CO} - K_{CO2(CO)} \cdot P_{CO2})/(1 - K_{CO2(CO)} \cdot K_{CO(CO2)})$$

$$Q_{CO2} = (P_{CO2} - K_{CO(CO2)} \cdot P_{CO})/(1 - K_{CO(CO2)} \cdot K_{CO2(CO)})$$

Q: the second-order correction value (correction value wherein mutual interference between CO and $CO_2$ is excluded)

$K_{CO(CO2)}$: the interference correction coefficient by CO to the accrual measurement value of $CO_2$ $K_{CO2(CO)}$: the interference correction coefficient by $CO_2$ to the accrual measurement value of CO Next, thus obtained $Q_{CO}$, $Q_{CO2}$, $P_{H2O}$ are provided with a zero/span calibration process and a linearlization process. Each value (an intermediate correction value) is set to be $S_{CO}$, $S_{CO2}$, $S_{H2O}$ respectively.

Next, moisture interference at a zero point is corrected to the intermediate correction values $S_{CO}$, $S_{CO2}$ by the use of the intermediate correction value $S_{H2O}$. The correction equation is as follows.

$$T_{CO} = S_{CO} - K_{H2O0(CO)} \cdot S_{H2O}$$

$$T_{CO2} = S_{CO2} - K_{H2O0(CO2)} \cdot S_{H2O}$$

T: the value wherein moisture interference at a zero point is corrected $K_{H2O0(CO)}$: the moisture interference correction coefficient of CO $K_{H2O0(CO2)}$: the moisture interference correction coefficient of $CO_2$ Furthermore, the moisture coexistence influence at the span point is corrected. The correction equation is as follows.

$$U_{CO} = T_{CO}/(1 - K_{H2O1(CO)} \cdot S_{H2O})$$

$$U_{CO2} = T_{CO2}/(1 - K_{H2O1(CO2)} \cdot S_{H2O})$$

U: the value wherein moisture coexistence influence at a span point is corrected $K_{H2O1(CO)}$: the moisture coexistence influence correction coefficient of CO $K_{H2O1(CO2)}$: the moisture coexistence influence correction coefficient of $CO_2$ Later, the concentration of CO and the concentration of $CO_2$ in the semi-dry state are calculated by providing $U_{CO}$, $U_{CO2}$ and $S_{H2O}$ with a pressure compensation process and a temperature compensation process.

Next, the concentration of $NO_X$ will be explained.

The correction part 73 provides the actual measurement value by the CLD type $NO_X$ analyzer 6 with a zero/span calibration process and a linearlization process based on the actual measurement value $O_{NOX}$ of the concentration of THC obtained by the hydrogen flame ionization analyzer 5.

Next, the value is provided with quenching (quenching effect) correction by $CO_2$. The correction equation is as follows.

$$R_{NOX} = Q_{NOX}/(1 + K_{CO2} \cdot [CO_2 \text{conc. (vol \%)}])$$

$Q_{NOX}$: the value wherein zero/span calibration is provided with the actual measurement value $O_{NOX}$ $K_{CO2}$: the $CO_2$ interference (quenching) correction coefficient

[$CO_2$conc. (vol %)]: the concentration of $CO_2$ (semi-dry state)

Next, the value is provided with quenching (quenching effect) correction by $H_2O$. The correction equation is as follows.

$$U_{NOX} = R_{NOX}/(1 + K_{H2O} \cdot [H_2O \text{ conc. (vol \%)}])$$

$K_{H2O}$: the $H_2O$ interference (quenching) correction coefficient

[$H_2O$ conc. (vol %)]: the concentration of $H_2O$ (semi-dry state)

Later, the concentration of $NO_X$ in the semi-dry state is calculated by providing the value of $U_{NOX}$ with a pressure compensation process and a temperature compensation process.

As mentioned above, the correction part 73 calculates the concentration of THC, the concentration of CO, the concentration of $CO_2$ and the concentration of $NO_X$ (final correction value) in the semi-dry state respectively and stores the data of each concentration in the semi-dry data storing part D2.

Next, the dry concentration calculating part 74 obtains each data stored in the semi-dry data storing part D2 and calculates the concentration of each component as the object to be measured in the exhaust gas in a dry state wherein moisture is completely removed. In order to convert the concentration in the semi-dry state into the concentration in the dry state, the following equation (1) is used.

$$X = W \cdot 100/(100 - [H_2O\text{conc. (vol \%)}]) \tag{1}$$

W: the concentration of the component as the object to be measured in a semi-dry state X: the concentration of the component as the object to be measured in a dry state

[$H_2O$conc. (vol %)]: concentration of $H_2O$ (semi-dry state)

The information processing unit 7 stores parameter data in the parameter data storing part D3 obtained by receiving data concerning an amount of moisture vapor in atmosphere, atmosphere temperature, atmosphere humidity and atmospheric pressure from each corresponding sensor, and receiving a hydrogen-carbon atom number ratio in fuel burned in an engine of a vehicle as an object to be tested by an input from an operator, or receiving a ratio of $NO_2$ in $NO_X$ from the CLD type $NO_X$ analyzer 6.

Next, the actual concentration calculating part 75 obtains the concentration of each component in a dry state from the semi-dry data storing part D2, obtains the parameter data that shows the amount of moisture vapor in the atmosphere, the atmosphere temperature, the atmosphere humidity, the atmospheric pressure, the hydrogen-carbon atom number ratio in the fuel, and the ratio of $NO_2$ in $NO_X$ from the parameter data storing part D3, and calculates the concentration of each component in the dry state wherein moisture is completely removed based on a predetermined conversion equation.

As the above-mentioned conversion equation, an officially-known conversion equation can be used, for example, a dry to wet conversion equation expressed by the following series of equations described in CFR-1065.

$$C_{EXCOMP}(t) = C_{EXCOMP\_dry}(t) \times (1 - C_{H2O}(t)) C_{H2O}$$
$$(t) = C_{H2O\_dry}(t)/(1 + C_{H2O\_dry}(t)) C_{H2O\_dry}(t) = \alpha/2 \times$$
$$X_{Oproddry}(t) + X_{H2Oint\ dry}(t)/X_{prod/int\ dry}(t) X_{Oproddry}$$
$$(t) = C_{EXCO2\_dry}(t + DT_{CO2})/100 + C_{EXCO\_dry}(t +$$
$$DT_{CO})/100 + C_{EXHC\_dry}(t + DT_{HC})/$$
$$1000000 X_{prod/int\ dry}(t) = 1/\{1 - \frac{1}{2} \times (C_{EXCO\_dry}(t +$$
$$DT_{CO})/100 - \alpha/2 \times X_{Cproddry} - C_{EXNO2\_dry}(t +$$
$$DT_{NO2})/1000000)\} C_{EXNO2\_dry}(t) = C_{EXNOx\_dry}$$
$$(t) \times FNO\ X_{H2Oint\ dry}(t) = X_{H2Oint}/(1 - X_{H2Oint}) X_{H2Oint}$$
$$(t) = EXP\{-6096.9385/(T_{AMB}(t) + 273.15) +$$
$$21.2409642 - 2.711193 \times 10^{-2} \times (T_{AMB}(t) + 273.15) +$$
$$1.673952 \times 10^{-5} \times (T_{AMB}(t) + 273.15)^2 + 2.433502 \times$$
$$Ln(T_{AMB})(t) + 273.15)\} \times RH_{AMB}(t)/(P_{AMB}(t) \times$$
$$1000 \times 100)$$

Here, each parameter in the above equations is as follows.

$C_{EXCOMP}(t)$; the momentary emission concentration after the wet conversion at the time t (CO, $CO_2$; vol %, THC, $NO_X$; ppm)

$C_{EXCOMP\_dry}(t)$; the momentary emission concentration in the dry state at the time t (measurement value)(CO, $CO_2$; vol %, THC, $NO_X$; ppm)

$C_{H2O}(t)$; the ratio of moisture in the exhaust gas at the time t $C_{H2O\_dry}(t)$; the ratio of moisture in the exhaust gas after the dry conversion at the time t α; the hydrogen-carbon atom number ratio in the fuel FNO; the ratio of $NO_2$ in $NO_X$ (gasoline; 1, diesel; 0.25, $NO_2$ occluded catalytic agent; 0.75)

$\chi_{H2Oint}(t)$; the amount of moisture vapor in the atmosphere at the time t (mol/mol)

$T_{AMB}(t)$; the atmosphere temperature at the time t (degC)

$RH_{AMB}(t)$; the atmosphere humidity at the time t (RH %)

$P_{AMB}(t)$; the atmospheric pressure at the time t (KPa)

In brief, this conversion equation is an equation that can calculate a ratio of $H_2O$ contained in the exhaust gas in the dry state from the given hydrogen-carbon atom number ratio contained in the fuel and the measured and calculated concentration of each component in the dry state and that can convert it into the concentration of each component as the object to be measured contained in the exhaust gas in a wet state of the exhaust gas, namely at a time when the exhaust gas is discharged, based on the calculated ratio of $H_2O$. The concentration of the component as the object to be measured contained in the exhaust gas at the time when the exhaust gas is discharged can be calculated from the concentration of each component measured by the measuring instrument group in the semi-dry state by the use of the conversion equation described in CFR-1065 and the equation that converts the concentration in the semi-dry state into the concentration in the dry state.

As mentioned above, in accordance with this embodiment, since interference or quenching of the components as the object to be measured by each analyzer 4, 5, 6 is mutually corrected by the use of the measurement value, there is no need of providing a detector for correction for exclusive use, thereby to downsize the exhaust gas analyzer and to save electric power.

In addition, since the CLD type $NO_X$ analyzer 6 does not need a process of diminishing the flow rate of the exhaust gas to import in order to reduce quenching due to $CO_2$ or $H_2O$ nor a process of diluting the exhaust gas in advance, the flow rate of the exhaust gas importing to the CLD type $NO_X$ analyzer 6 can be increased at once, thereby to improve sensitivity. Furthermore, since the CLD type $NO_X$ analyzer 6 is arranged on the main flow path 1 (bypass) and there is no need of providing a flow path exclusive for the CLD type $NO_X$ analyzer 6 by making use of the arrangement wherein the flow rate of the exhaust gas importing to the CLD type $NO_X$ analyzer 6 can be increased, this arrangement contributes to downsizing also on this point.

In addition, since high vacuum is unnecessary, the vacuum pump 19 can be downsized. Furthermore, the capillaries 15a, 15b, 21, 31 and the pressure control valve 17a, 17b are arranged on the main flow path 1 or the sub-flow paths 2, 3 so that it is possible for a single vacuum pump 19 to control the flow rate and the pressure of the exhaust gas importing to each analyzer 4, 5, 6, thereby to downsize the exhaust gas analyzer and to save electric power.

Furthermore, it is possible for the infrared gas analyzer 4 not to require a dehumidifier or to downsize a dehumidifier to reduce the moisture interference influence, thereby to downsize the exhaust gas analyzer and to save electric power.

The arrangement of using the unheated piping makes it possible to reduce electric consumption, which significantly contributes to power saving.

In addition, in this embodiment, since the sub-flow paths 2, 3 are arranged from the bifurcated part 16 of the main flow path 1 so that the exhaust gas can be introduced into each analyzer 4, 5, 6 as quickly as possible and at the same time as much as possible and the information processing unit 7 corrects difference of the time when the exhaust gas reaches each analyzer 4, 5, 6, the response of measurement is excellent. As a result, it is possible to measure the concentration of the component as the object to be measured in the exhaust gas continuously and accurately.

As a result of the arrangement of this embodiment, it is possible to realize the exhaust gas analyzer 100 of a vehicle-mountable type that can conduct a measurement continuously on a real time basis and that is superior in accuracy of measurement.

The present claimed invention is not limited to the above-mentioned embodiment. The method or the arrangement for correcting interference or quenching may be conceived otherwise and the analyzer may be of other type. It is not limited to the vehicle-mountable type, and may be of a stand-alone type such as used in a laboratory. In this case also, the same operation and effect can be produced as that of the above-mentioned embodiment.

The other arrangement of the component is not limited to the embodiment described in drawings and there may be various modifications without departing from the spirit of the invention.

In accordance with this invention, it is possible to provide the exhaust gas analyzer 100 that is downsized, electric power saved, and high in sensitivity and that can conduct measurement continuously on a real time basis. Especially, this invention makes it possible to provide the exhaust gas analyzer 100 that is preferable for mounting on a vehicle.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. An exhaust gas analyzer comprising:
   a main flow path to which exhaust gas discharged from an internal combustion engine is continuously introduced in a chronological order and which acts as a common bypath to pass at least a portion of the exhaust gas;
   at least one sub-flow path furcated from the main flow path and arranged in parallel to the main flow path;
   plural kinds of analyzers some of which are mounted on the main flow path and others of which are mounted on the at least one sub-flow path, and that measure concentration of each of multiple components in the exhaust gas in a chronological order, the plural kinds of analyzers including an infrared gas analyzer mounted on the main flow path to measure concentrations of CO, $CO_2$ and $H_2O$, a hydrogen flame ionization analyzer mounted on the at least one sub-flow path to measure a concentration of THC and a chemiluminescence nitrogen oxide analyzer mounted on the at least one sub-flow path to measure a concentration of $NO_X$;
   an information processing unit having a memory for storing a difference of time between times until the exhaust gas reaches each analyzer;
   an actual measurement value obtaining part that obtains an actual measurement value of the concentration for each measured component in the exhaust gas discharged at the same time by obtaining an actual measurement value of the concentration for each measured component in the exhaust gas that reaches one of the plural kinds of analyzers at a latest time and another actual measurement value of the concentration for each measured component in the exhaust gas that reaches another one of the plural kinds of analyzers at a time prior to the latest time by a deviance of time when the actual measurement value of the concentration for each measured component in the exhaust gas is obtained from the one of the plural kinds of analyzers; and
   a correction part that corrects a deviance from a true value generated to an actual measurement value due to a mutual influence of the measured components based on at least one actual measurement value.

2. The exhaust gas analyzer of claim 1, wherein the correction part conducts intermediate correction on each actual measurement value concerning the concentration of CO, the concentration of $CO_2$, and the concentration of $H_2O$ based on the actual measurement value of the concentration of THC obtained by the hydrogen flame ionization analyzer, and the intermediate correction value of the concentration of CO and the intermediate correction value of the concentration of $CO_2$ are further corrected based on the intermediate correction value of the concentration of CO, the intermediate correction value of the concentration of $CO_2$ and the intermediate correction value of the concentration of $H_2O$.

3. The exhaust gas analyzer of claim 2, wherein the correction part corrects the actual measurement value concerning the concentration of $NO_X$ based on a final correction value of the concentration of $CO_2$ and a final correction value of the concentration of $H_2O$.

4. The exhaust gas analyzer of claim 1, wherein a downstream end of the main flow path and downstream ends of the sub-flow paths are arranged to be sucked by a common pump.

5. The exhaust gas analyzer of claim 1 wherein the exhaust gas analyzer is of a vehicle-mountable type.

6. A vehicle-mountable exhaust gas analyzer that is of a vehicle-mountable type that measures concentration of a component such as $NO_X$, THC, CO and $CO_2$ contained in exhaust gas discharged from a vehicle, and that comprises:
   a drain separator connected to an exhaust duct of the vehicle through an unheated piping without a chiller that consumes electric power wherein the exhaust gas discharged from the vehicle is cooled by the unheated piping and wherein moisture contained in the exhaust gas is condensated inside the unheated piping and is discharged out of the unheated piping through the drain separator;
   a measuring instrument group that measures concentration of moisture in the exhaust gas and concentration of the measured component in a semi-dry state wherein liquid moisture is removed by the drain separator;
   a dry concentration calculating part that calculates concentration of the measured component in the exhaust gas in a dry state wherein moisture is completely removed based on the concentration of the moisture and the concentration of the measured component obtained by the measuring instrument group; and
   an actual concentration calculating part that calculates concentration of the measured component contained in the exhaust gas at a time when the exhaust gas is discharged from the vehicle based on the concentration of the component in the dry state and a predetermined conversion equation.

7. A vehicle-mountable exhaust gas analyzer that is of a vehicle-mountable type that measures concentration of a component such as $NO_X$, THC, CO and $CO_2$ contained in exhaust gas discharged from a vehicle, and that comprises:
   a drain separator connected to an exhaust duct of the vehicle through an introductory piping that is made from an unheated piping without a chiller that consumes electric power wherein the exhaust gas discharged from the vehicle is cooled by the introductory piping and wherein moisture contained in the exhaust gas is condensated inside the introductory piping and is discharged out of the introductory piping through the drain separator;

a measuring instrument group that includes an infrared gas analyzer to measure concentration of CO, concentration of $CO_2$ and concentration of $H_2O$, a chemiluminescence nitrogen oxide analyzer to measure concentration of $NO_X$, and a hydrogen flame ionization detector to measure concentration of THC, and that measures concentration of the measured component in the exhaust gas in a semi-dry state wherein liquid moisture is removed by the drain separator;

a dry concentration calculating part that calculates concentration of the measured component in the exhaust gas in a dry state wherein moisture is completely removed based on the concentration of the measured component and the concentration of $H_2O$ measured by the measuring instrument group; and an actual concentration calculating part that calculates concentration of the measured component contained in the exhaust gas at a time when the exhaust gas is discharged from the vehicle based on the concentration of the component in the dry state and a predetermined conversion equation.

8. The vehicle-mountable exhaust gas analyzer of claim 6 further comprising:

a correction part that corrects a deviance from a true value generated to an actual measurement value due to a mutual influence of the measured components based on at least one actual measurement value and that calculates true measurement value of the measured component in a semi-dry state; and wherein the dry concentration calculating part calculates the concentration of each measured component in the dry state based on the true measurement value obtained by the correction part.

9. The vehicle-mountable exhaust gas analyzer of claim 8, wherein the correction part conducts intermediate correction on each actual measurement value concerning the concentration of CO, the concentration of $CO_2$, and the concentration of $H_2O$ based on the actual measurement value of the concentration of THC obtained by the hydrogen flame ionization analyzer, and the intermediate correction value of the concentration of CO and the intermediate correction value of the concentration of $CO_2$ are further corrected based on the intermediate correction value of the concentration of CO, the intermediate correction value of the concentration of $CO_2$ and the intermediate correction value of the concentration of $H_2O$; and wherein the correction part calculates a true measurement value for each measured component in the semi-dry state by correcting the actual measurement value concerning the concentration of $NO_X$ based on the correction value of the concentration of $CO_2$ and the correction value of the concentration of $H_2O$.

* * * * *